United States Patent [19]

Ting et al.

[11] Patent Number: 5,574,173

[45] Date of Patent: Nov. 12, 1996

[54] TRICYCLIC DERIVATIVES, COMPOSITIONS AND METHODS OF USE

[75] Inventors: Pauline C. Ting, New Providence; Richard J. Friary, Bridgewater; Wing C. Tom, Cedar Grove, all of N.J.; Joe F. Lee, Brooklyn, N.Y.; Vera A. Seidl, Wayne, N.J.

[73] Assignee: Schering Corporation, Kenilworth, N.J.

[21] Appl. No.: 162,686

[22] Filed: Dec. 6, 1993

[51] Int. Cl.[6] .................. C07D 313/10; C07C 211/31; A61K 31/335; A61K 31/135

[52] U.S. Cl. .................................... 549/354; 564/427

[58] Field of Search .............. 549/354, 12; 514/450, 514/431, 656, 290, 291; 564/427, 379, 380; 546/93, 89

[56] References Cited

U.S. PATENT DOCUMENTS

| | | | |
|---|---|---|---|
| 3,372,196 | 3/1968 | Engelhardt | 260/570.8 |
| 3,438,981 | 4/1969 | Stach | 549/354 |
| 3,535,315 | 10/1970 | Winter et al. | 549/354 |
| 3,595,865 | 7/1971 | Sorenson et al. | 546/285 |
| 3,639,423 | 2/1972 | Winter et al. | 549/354 |
| 3,674,841 | 7/1972 | Boissier et al. | 564/379 |
| 3,922,305 | 11/1975 | Engelhardt | 260/570.8 |
| 3,927,128 | 12/1975 | Kyburz et al. | 564/380 |
| 3,944,566 | 3/1976 | Winter et al. | 549/26 |
| 3,965,181 | 6/1976 | Marx | 564/345 |
| 3,978,121 | 8/1976 | Engelhardt | 260/551 C |
| 3,981,917 | 9/1976 | Englehardt | 260/570.8 |
| 3,991,103 | 11/1976 | Barton et al. | 564/379 |
| 4,070,373 | 1/1978 | Winter et al. | 549/354 |
| 4,496,557 | 1/1985 | Malen et al. | 514/450 |
| 4,585,788 | 4/1986 | Helsey et al. | 514/450 |
| 4,626,542 | 12/1986 | King et al. | 514/325 |
| 4,645,758 | 2/1987 | Willman et al. | 549/354 |
| 4,826,853 | 5/1989 | Piwinski et al. | 514/290 |
| 4,996,321 | 2/1991 | Baldwin et al. | 546/194 |
| 5,089,496 | 2/1992 | Piwinski et al. | 514/253 |
| 5,104,876 | 4/1992 | Piwinski et al. | 514/254 |
| 5,140,027 | 8/1972 | Ong et al. | 514/450 |
| 5,151,423 | 9/1992 | Piwinski et al. | 514/254 |

FOREIGN PATENT DOCUMENTS

| | | |
|---|---|---|
| 0235796 | 9/1987 | European Pat. Off. . |
| 0341860 | 4/1989 | European Pat. Off. . |
| 0487502 | 5/1992 | European Pat. Off. . |
| 0515158A1 | 11/1992 | European Pat. Off. . |
| 0589038 | 3/1994 | European Pat. Off. . |
| 6009609 | 1/1994 | Japan . |
| 1018995 | 2/1966 | United Kingdom . |
| 1274262 | 5/1992 | United Kingdom . |
| 88/03138 | 5/1988 | WIPO . |
| 89/10363 | 11/1989 | WIPO . |
| 89/10369 | 11/1989 | WIPO . |
| WO92/11034 | 7/1992 | WIPO . |

OTHER PUBLICATIONS

Chem. Abstracts Reg. No. 55286–80–1 (1992).
Chem. Abstracts Reg. No. 23509–37–7 (1992).
Chem. Abstracts Reg. No. 23485–60–1 (1992).
Chem. Abstracts Reg. No. 138729–88–1 (1993).
Chem. Abstracts Reg. No. 138707–21–8 (1993).
Chem. Abstracts Reg. No. 37028–07–2 (1993).

*Primary Examiner*—Richard L. Raymond
*Assistant Examiner*—Deborah Lambkin
*Attorney, Agent, or Firm*—James M. Gould

[57] ABSTRACT

Disclosed are compounds of Formula I:

(I)

or a pharmaceutically acceptable salt or solvate thereof, wherein:

$R^4$ is alkenyl, alkoxy, or —OH.

Also disclosed are pharmaceutical compositions containing compounds of Formula I, methods for inhibiting tumor necrosis factor-α, and methods for treating septic shock, inflammation, or allergic disease.

21 Claims, No Drawings

TRICYCLIC DERIVATIVES, COMPOSITIONS AND METHODS OF USE

FIELD OF THE INVENTION

The present invention relates to tricyclic derivatives, pharmaceutical compositions and methods of using such derivatives. The compounds of the present invention inhibit tumor necrosis factor α ("TNF-α").

BACKGROUND OF THE INVENTION

Tumor necrosis factor α ("TNF-α") is a polypeptide cytokine known to induce a variety of inflammatory and metabolic processes in vivo. See, e.g., *Ann. Rev. Immunol.* 7:625 (1989). However, overproduction or inappropriate production of TNF-α has been shown to be involved in several pathological conditions, including septic shock and various allergic diseases and inflammatory conditions. See, e.g., *Immunol. Res.* 10:122 (1991), *Science* 229:869 (1985) and *Proc. Natl. Acad. Sci.* 89:7375 (1992). Thus, compounds that could inhibit TNF-α would be quite valuable in treating these conditions.

In view of the substantial interest in agents that inhibit TNF-α, the identification of compounds having anti-TNF-α activity would be a valuable contribution to the art. This invention provides just such a contribution by providing novel compounds having anti-TNF-α activity. In addition, this invention provides methods of using such compounds.

SUMMARY OF THE INVENTION

We have now unexpectedly found that compounds having the general formula I (set forth below) provide surprisingly good activity as inhibitors of tumor necrosis factor α (TNF-α). More specifically, we believe that the compounds of formula I provide this activity by inhibiting the biosynthesis of TNF-α. In view of this surprising anti-TNF-α activity, it is believed that compounds of formula I are useful in the relief of septic shock, allergic diseases, and inflammatory conditions.

Formula I is as follows:

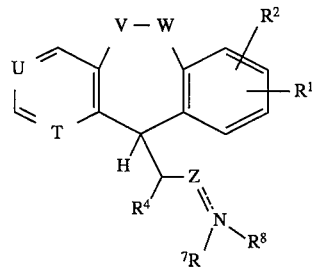

or a pharmaceutically acceptable salt or solvate thereof, wherein:

one of T and U represents N and the other represents =CH—; or each of T and U represents =CH—;

one of V and W represents oxygen and the other represents —CH$_2$—; or each of V and W represents —CH$_2$—;

$R^1$ and $R^2$ are each independently selected from the group consisting of H and halogen;

$R^4$ is alkenyl, alkoxy, or —OH;

Z --- N represents an optional double bond;

when Z === N is a double bond, Z represents —CH=, or —CH$_2$C(R$^5$)=, wherein $R^5$ is H or lower alkyl; and $R^7$ and $R^8$ together represent OR$^9$;

when Z === N represents a single bond, Z represents —CH$_2$—, —CH=CH—, or —CH$_2$C(R$^5$)(R$^6$)—, wherein $R^5$ and $R^6$ are independently H or lower alkyl; and $R^7$ and $R^8$ are independently H, alkyl, alkenyl, alkynyl, aryl, alkaryl, aralkyl, cycloalkyl, —OR$^9$; —C(O)OR$^{10}$; —CH$_2$C(O)OR$^9$; —C(O)R$^{10}$; —SO$^2$R$^{10}$; —CO-4-pyridyl-N-oxide; —(CH$_2$)$_n$—N(CH$_3$)$_2$, where n is 2 to 4; —(CH$_2$)$_m$O(CH$_2$)$_j$OH, where m and j are independently 2 or 3;

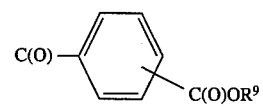

or $R^7$ and $R^8$ together form either a five-membered or a six-membered ring optionally substituted with COOR$^9$; a six-membered ring containing NR$^{10}$; or a five-membered ring fused to a benzene ring;

$R^9$ is H or lower alkyl; and $R^{10}$ is alkyl or aryl.

More preferred compounds of this invention are represented by Formula I wherein $R^4$ is alkoxy, and more preferably wherein $R^4$ is ethoxy.

More preferred compounds also include those of Formula I wherein $R^4$ is alkenyl.

More preferred compounds also include those of Formula I wherein each of T and U represents =CH—.

More preferred compounds also include those of Formula I wherein $R^7$ and $R^8$ are independently H, alkyl, alkenyl, alkynyl, aryl, alkaryl, or aralkyl. Further, when $R^7$ and $R^8$ and N taken together form either a five-membered ring, a six-membered ring, or a five-membered ring fused to a benzene ring, the portion of the 5- or 6-membered ring represented by $R^7$ and $R^8$ is preferably carbocyclic optionally having a nitrogen atom substituted for one of the carbon atoms.

Representative compounds of this invention include, but are not limited to:

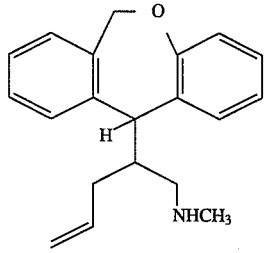

(IA)

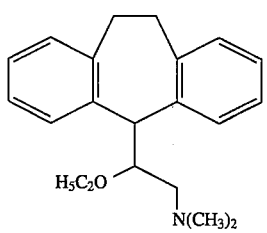

(IB)

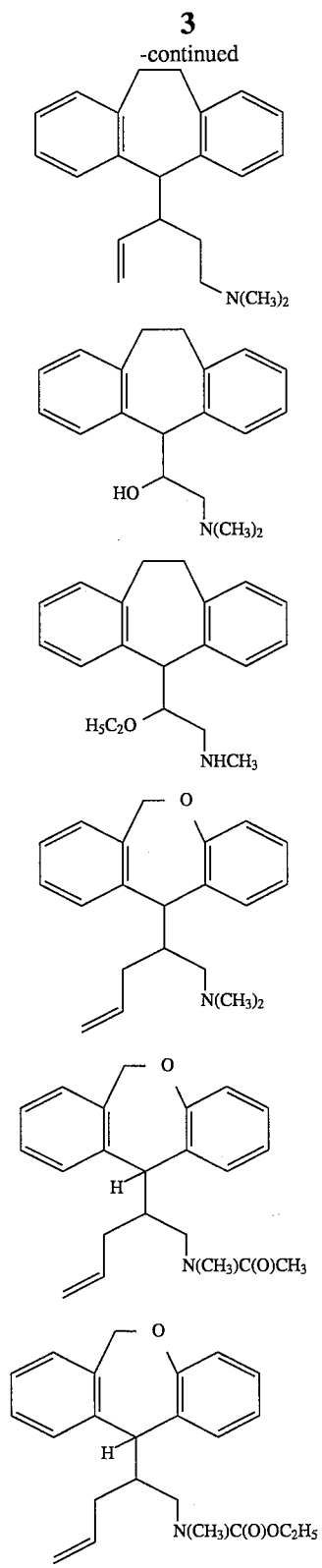

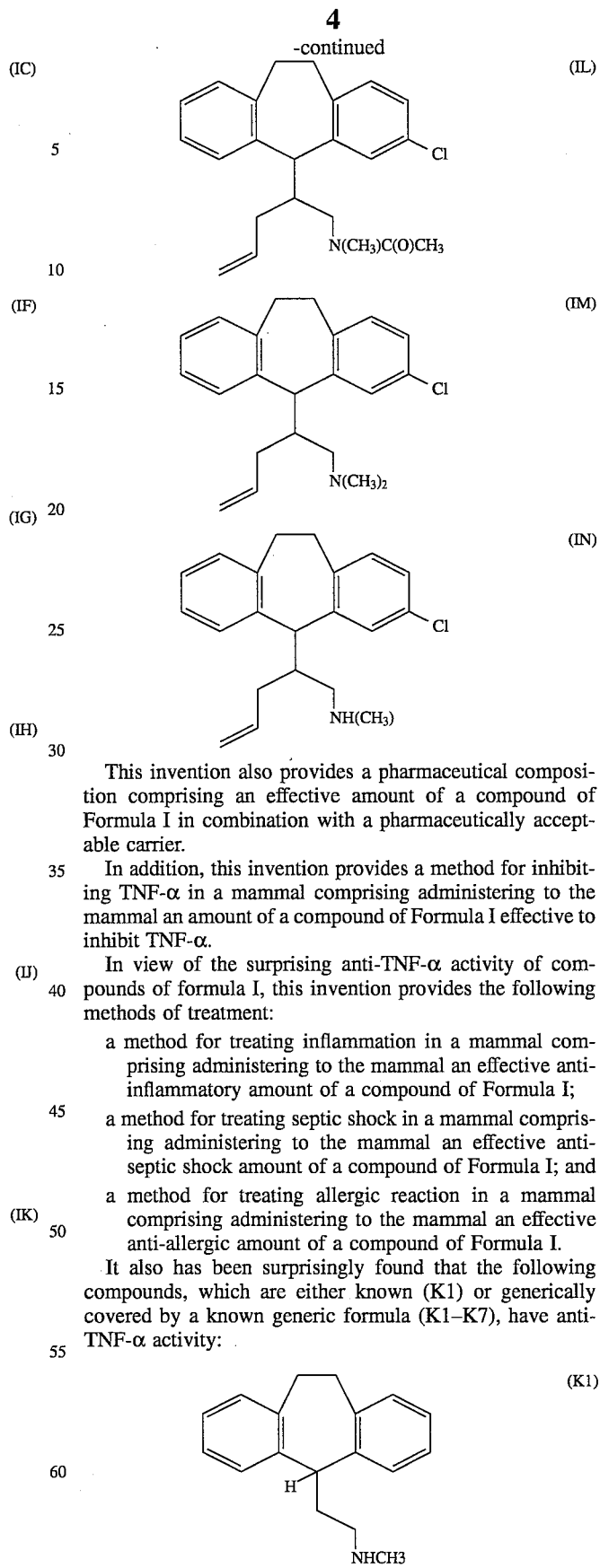

This invention also provides a pharmaceutical composition comprising an effective amount of a compound of Formula I in combination with a pharmaceutically acceptable carrier.

In addition, this invention provides a method for inhibiting TNF-α in a mammal comprising administering to the mammal an amount of a compound of Formula I effective to inhibit TNF-α.

In view of the surprising anti-TNF-α activity of compounds of formula I, this invention provides the following methods of treatment:

a method for treating inflammation in a mammal comprising administering to the mammal an effective anti-inflammatory amount of a compound of Formula I;

a method for treating septic shock in a mammal comprising administering to the mammal an effective anti-septic shock amount of a compound of Formula I; and a method for treating allergic reaction in a mammal comprising administering to the mammal an effective anti-allergic amount of a compound of Formula I.

It also has been surprisingly found that the following compounds, which are either known (K1) or generically covered by a known generic formula (K1–K7), have anti-TNF-α activity:

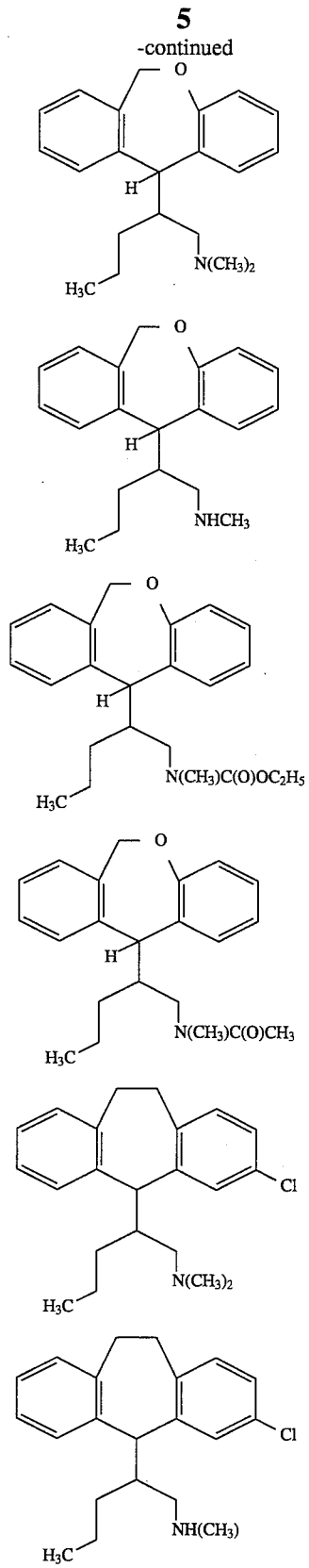

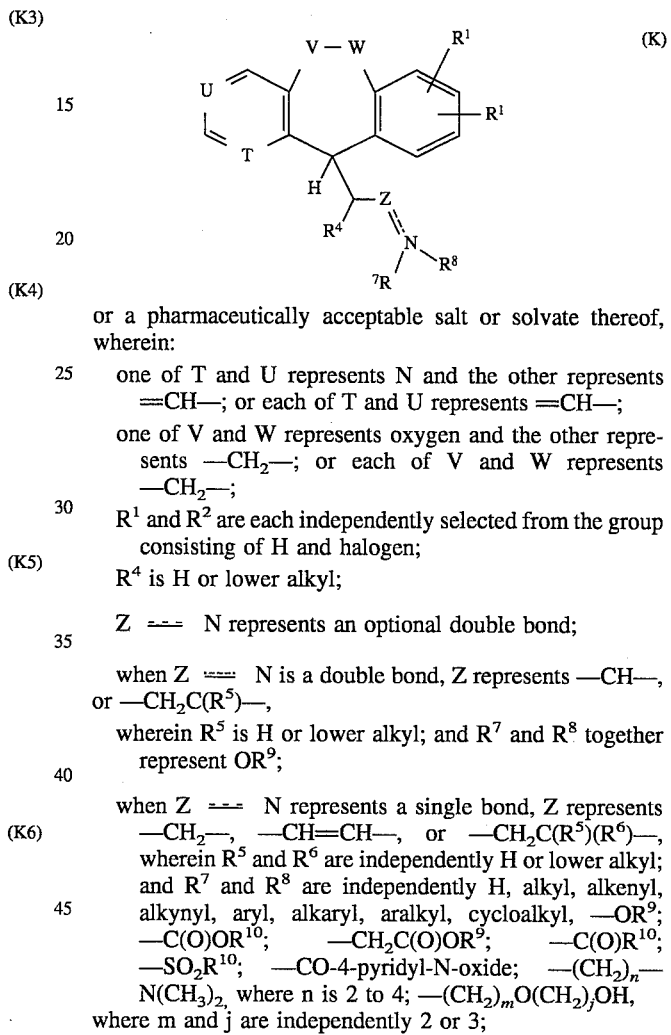

With regard to the above-listed compounds, prior to the present application compound K1 was only disclosed as having activity as an anti-depressant. See Protiva et al, J. Med. Pharm. Chem. 4, 411 (1961); Winter et al, German Patent Publication 2335943 (1975). The generic formula covering compounds K2–K7 (as well as K1) has only been disclosed as having cardiac and circulatory activity. See U.S. Pat. No. 4,070,373 (1978) to Winter et al.

Thus, in view of the surprising anti-TNF activity of the above-mentioned compounds K1–K7, this invention also provides methods of using these compounds to treat a mammal for inflammation, septic shock, and allergic reaction. Accordingly, the present invention also provides methods of using compounds of formula K (set forth below) for inhibiting TNF-α and for treating a mammal for inflammation, septic shock, and allergic reaction.

Formula K is as follows:

or a pharmaceutically acceptable salt or solvate thereof, wherein:

one of T and U represents N and the other represents =CH—; or each of T and U represents =CH—;

one of V and W represents oxygen and the other represents —CH$_2$—; or each of V and W represents —CH$_2$—;

R$^1$ and R$^2$ are each independently selected from the group consisting of H and halogen;

R$^4$ is H or lower alkyl;

Z --- N represents an optional double bond;

when Z === N is a double bond, Z represents —CH—, or —CH$_2$C(R$^5$)—,
  wherein R$^5$ is H or lower alkyl; and R$^7$ and R$^8$ together represent OR$^9$;

when Z --- N represents a single bond, Z represents —CH$_2$—, —CH=CH—, or —CH$_2$C(R$^5$)(R$^6$)—, wherein R$^5$ and R$^6$ are independently H or lower alkyl; and R$^7$ and R$^8$ are independently H, alkyl, alkenyl, alkynyl, aryl, alkaryl, aralkyl, cycloalkyl, —OR$^9$; —C(O)OR$^{10}$; —CH$_2$C(O)OR$^9$; —C(O)R$^{10}$; —SO$_2$R$^{10}$; —CO-4-pyridyl-N-oxide; —(CH$_2$)$_n$—N(CH$_3$)$_2$, where n is 2 to 4; —(CH$_2$)$_m$O(CH$_2$)$_j$OH, where m and j are independently 2 or 3;

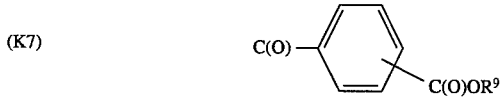

or R$^7$ and R$^8$ together form either a five-membered or a six-membered ring optionally substituted with COOR$^9$; a six-membered ring containing NR$^{10}$; or a five-membered ring fused to a benzene ring;

R$^9$ is H or lower alkyl; and

R$^{10}$ is alkyl or aryl.

In a more preferred embodiment for Formula K, Z === N represents a single bond and R$^7$ and R$^8$ are independently H or alkyl.

The present invention will be described in detail below in connection with several preferred embodiments. However, additional embodiments of the present invention will be apparent to those having ordinary skill in the art.

DETAILED DESCRIPTION OF THE INVENTION

As used herein, the following terms are used as defined below unless otherwise indicated:

alkyl—(including the alkyl portions of alkoxy and cycloalkyl)—represents straight and branched carbon chains and contains from one to twenty carbon atoms, preferably one to six carbon atoms;

alkenyl—(including the alkenyl portions of cycloalkenyl) represents straight and branched carbon chains having at least one carbon to carbon double bond and containing from 2 to 12 carbon atoms, preferably from 2 to 6 carbon atoms;

alkynyl—represents straight and branched carbon chains having at least one carbon to carbon triple bond and containing from 2 to 12 carbon atoms, preferably from 2 to 6 carbon atoms;

aryl—represents a carbocyclic group (preferably phenyl or substituted phenyl) containing from 6 to 14 carbon atoms and having at least one phenyl or fused phenylene ring, with all available substitutable carbon atoms of the carbocyclic group being intended as possible points of attachment, said carbocyclic group being optionally substituted with one or more of halo, alkyl, hydroxy, alkoxy, phenoxy, cyano, cycloalkyl, alkenyloxy, alkynyloxy, —SH, —S(O)$_e$R$^{12}$ (wherein e is 1 or 2 and R$^{12}$ is alkyl or aryl), —CF$_3$, amino, alkylamino, dialkylamino, —COOR$^{12}$ or —NO$_2$;

acyl—(including the acyl portions of acyloxy) represents —C(O)—alkyl, —C(O)—alkenyl, —C(O)—alkynyl, —C(O)—cycloalkyl, —C(O)cycloalkenyl or —C(O)—cycloalkynyl;

alkaryl represents an aryl group, as defined above, in which an alkyl group, as defined above, is substituted for one of the aryl H atoms;

alkoxy—represents an alkyl group, as defined above, attached to a molecule through an oxygen molecule (—O—alkyl);

alkoxymethyl—represents an alkoxy group as defined above attached to a molecule through a methylene group;

aralkyl—represents an alkyl group, as defined above, in which an aryl group, as defined above, is substituted for one of the alkyl H atoms;

and halo—represents fluoro, chloro, bromo and iodo.

Certain compounds of the invention may exist in different isomeric (e.g., enantiomers and diastereoisomers) as well as conformational forms. The invention contemplates all such isomers both in pure form and in admixture, including racemic mixtures. Tautomeric forms are also included.

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

Lines drawn into the ring systems indicate that the indicated bond may be attached to any of the substitutable ring carbon atoms.

Certain compounds of the invention will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds of the invention also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The invention disclosed herein is exemplified by the following preparative examples, which should not be construed to limit the scope of the disclosure. Alternative synthetic pathways and analogous structures within the scope of the invention may be apparent to those of ordinary skill in the art. Further, those skilled in the art will recognize that the reactions are conducted under conditions, e.g., temperature, that will allow the reaction to proceed at a reasonable rate to completion. Unless indicated otherwise, the substituents for the formulas given hereinafter have the same definition as those of Formula I.

PREPARATIVE METHODS AND REACTION SCHEMES
Scheme 1

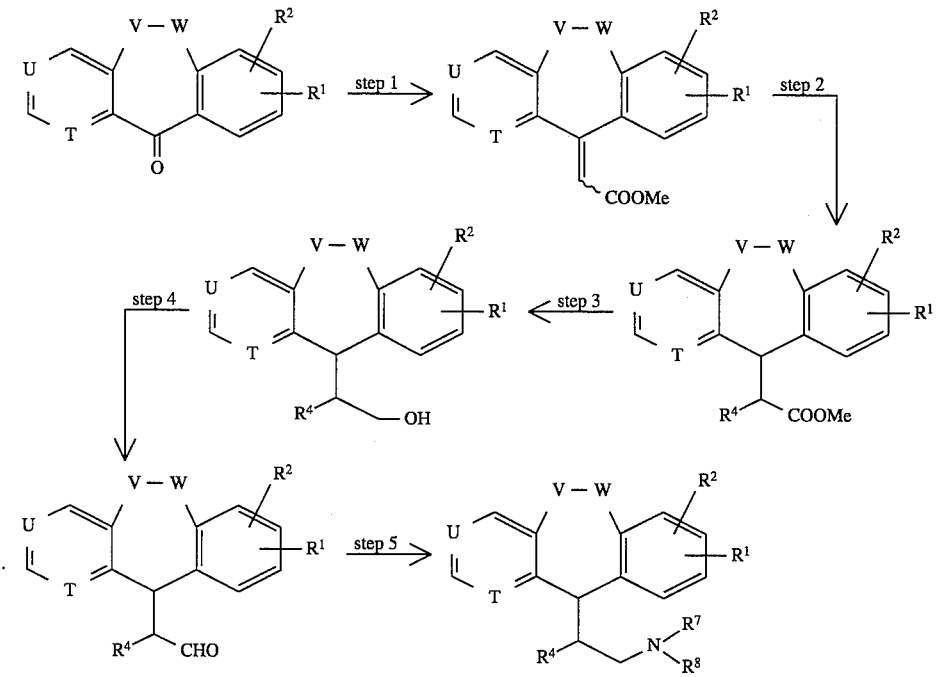

Step 1: This step is preferably carried out with the reagent trimethyl phosphonoacetate and sodium hydride in a polar aprotic solvent (e.g. N,N-dimethylformamide, N,N-dimethylacetamide, or dimethylsulfoxide) under an inert atmosphere (nitrogen or argon). Preferred temperature range is 25° C. to 80° C.

Step 2: This step is preferably carried out with a suitably substituted $R^4$ silyl reagent and tetra-n-butyl ammonium fluoride in an inert solvent such as a polar aprotic solvent (e.g. N,N-dimethylformamide or N,N-dimethylacetamide) with a cosolvent (e.g. 1,3-dimethyl-3,4,5,6-tetrahydro-2(1H)-pyrimidinone or hexamethylphosphoramide) under an inert atmosphere (nitrogen or argon). Preferred temperature range is between 25° C. and 80° C.

Step 3: This step is preferably carried out with any suitable reducing agent (e.g. diisobutylaluminum hydride, aluminum hydride, or lithium trimethoxyaluminum hydride) in an inert solvent such as ether (e.g. diethyl ether, tetrahydrofuran, or dioxane) at temperatures preferably between −78° C. and 25° C. under an inert atmosphere (nitrogen or argon).

Step 4: This step is preferably carried out with a suitable oxidizing agent (e.g. pyridinium chlorochromate, chromium trioxide-pyridine, pyridinium dichromate, oxalyl chloride-dimethylsulfoxide, acetic anhydride-dimethylsulfoxide, dicyclohexylcarbodiimide-dimethylsulfoxide, or periodinane) in an inert solvent such as chlorinated hydrocarbons (e.g. dichloromethane, 1,2-dichloroethane, or chloroform). Preferred temperature range is between −78° C. and 25° C.

Step 5: This step is preferably carried out with a suitably substituted amine (usually as its acid salt e.g. hydrochloride or maleate) and sodium cyanoborohydride in a solvent mixture of ether (e.g. diethyl ether, tetrahydrofuran, or dioxane) and protic solvent (e.g. methanol or ethanol) with 3A molecular sieves. Preferred temperature range is 25° C. to 70° C.

Scheme 2

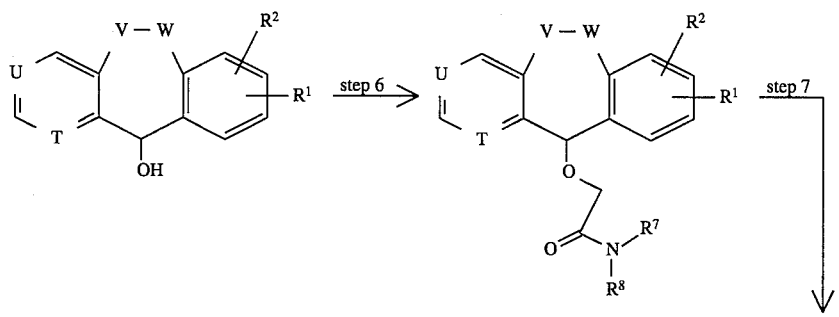

-continued
Scheme 2

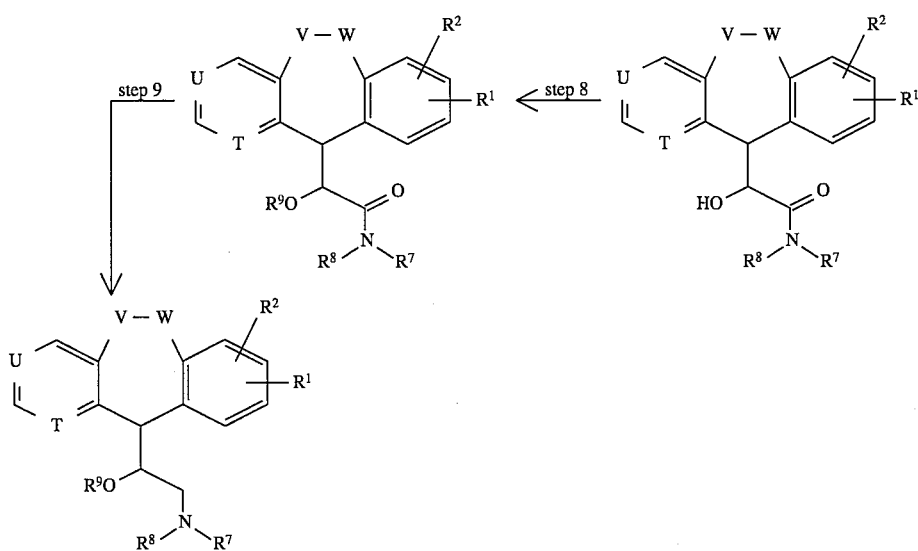

Step 6: This step is preferably carried out by first adding a base (e.g. sodium hydride, potassium hydride, or potassium bis(trimethylsilyl)amide) in an inert solvent (e.g. ether such as diethyl ether, tetrahydrofuran, or dioxane) under an inert atmosphere (nitrogen or argon). Subsequently, the alkylating reagent 2-chloro-N,N-dialkylacetamide is added, and the preferred temperature range is 25° C. to 65° C.

Step 7: This step is preferably carried out with a strong base (e.g. sodium hydride, potassium hydride, potassium bis(trimethylsilyl)amide, or lithium diisopropylamide) in an inert solvent (e.g. benzene or toluene) between 80° C. and 110° C. under an inert atmosphere (nitrogen or argon).

Step 8: This step is preferably carried out by first adding a base (e.g. sodium hydride or potassium hydride) in an inert solvent (e.g. ether such as tetrahydrofuran, dioxane, diglyme) under an inert atmosphere (nitrogen or argon). Subsequently, the alkylating agent $R^9L$ is added wherein L represents a good leaving group, e.g. L can be chloride, bromide, iodide, mesylate, or tosylate. Preferred temperature range is 70° C. to 160° C.

Step 9: This step is preferably carried out with any suitable reducing agent (e.g. lithium aluminum hydride, diborane, or aluminum hydride) in an inert solvent (e.g. ether such as diethyl ether, tetrahydrofuran, or dioxane) under an inert atmosphere (nitrogen or argon). Preferred temperatures range between 25° C. and 65° C.

Scheme 3

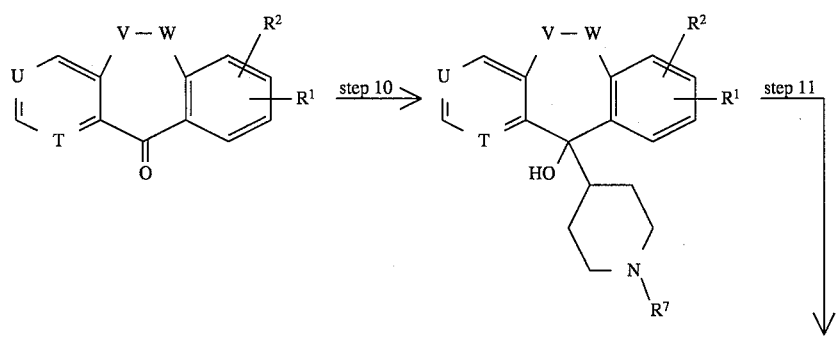

-continued
Scheme 3

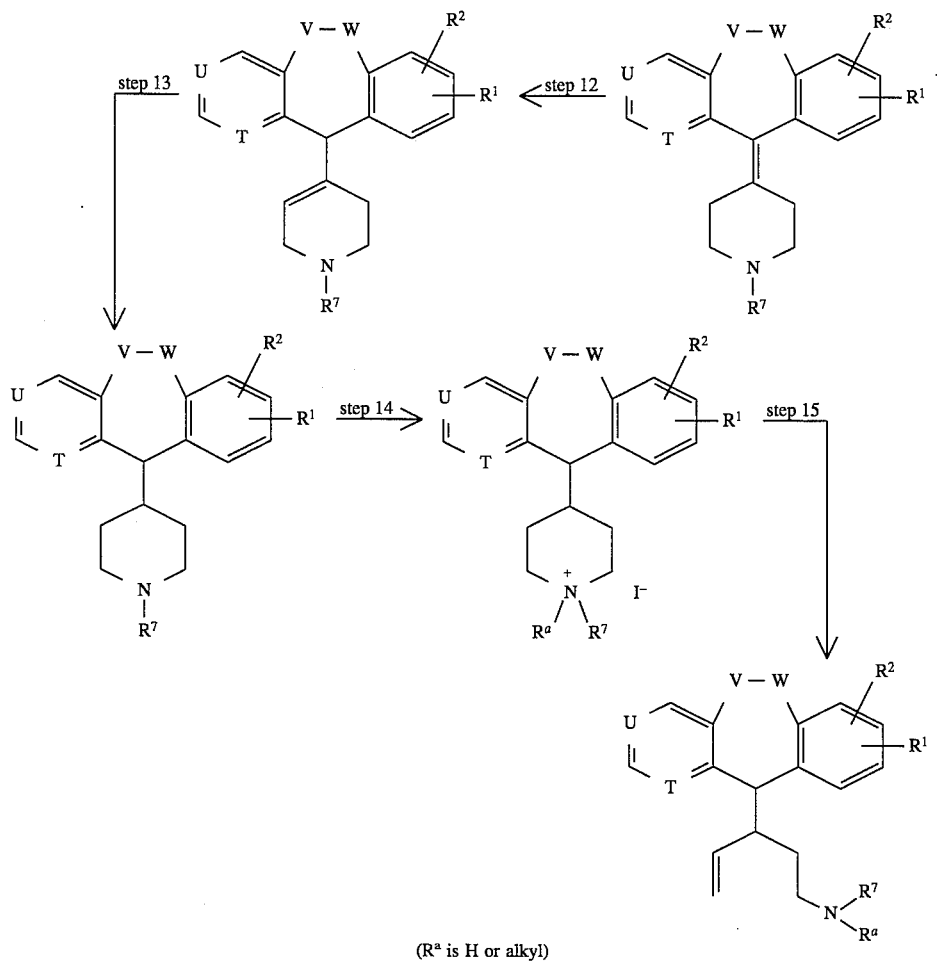

(R$^a$ is H or alkyl)

Step 10: This step is preferably carried out by adding the Grignard reagent of a suitably N-substituted 4-chloro-piperidine in an inert solvent such as ether (e.g. diethyl ether, tetrahydrofuran, or dioxane) under an inert atmosphere (nitrogen or argon). Preferred temperatures range between 0° C. and 60° C.

Step 11: This step is preferably carried out with strong acid (e.g. hydrochloric acid, sulfuric acid, or triflic acid) in water at temperatures between 25° C and 100° C.

Step 12: This step is preferably carried out by first adding a strong base (e.g. n-butyl lithium, sec-butyl lithium, or lithium diisopropylamide) in an inert solvent such as ether (e.g. diethyl ether, tetrahydrofuran, or dioxane) under an inert atmosphere (nitrogen or argon) at temperatures between −78° C and 0° C. Subsequently, a proton source (e.g. methanol, ethanol or acetic acid) is added.

Step 13: This step is preferably carried out by hydrogenation with a catalyst (e.g. palladium on carbon or platinum oxide) in an inert solvent (e.g. methanol, ethanol, ethyl acetate, or acetic acid) at 25° C.

Step 14: This step is preferably carried out by adding a methylating reagent (e.g. methyl chloride, methyl bromide, methyl iodide, methyl tosylate, or dimethyl sulfate) in an inert solvent such as a protic solvent (e.g. methanol, ethanol, isopropanol, or butanol) or a silylating agent (e.g. trimethylsilyl chloride, trimethylsilyl bromide, or trimethylsilyl iodide) in an inert solvent such as an ether (e.g. tetrahydrofuran). Preferred temperature is between 25° C. and 100° C.

Step 15: This step is preferably carried out by heating at high temperatures between 150° C. and 220° C.

GENERAL PROCESSES

Preparation of a compound of formula I wherein Z $=\!=\!=$ N represents a double bond A. 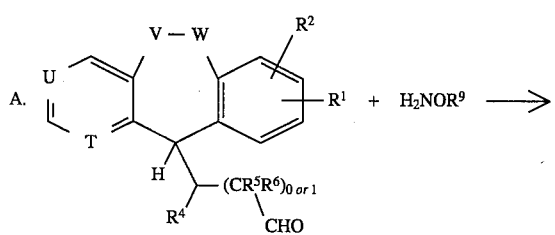 + H$_2$NOR$^9$ ⟶

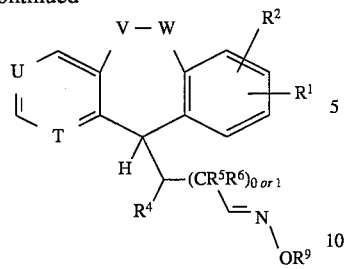

The process is preferably carried out by treating the aldehyde with a hydroxyl amine derivative in an inert solvent such as chlorinated hydrocarbons (e.g. dichloromethane, 1,2-dichloroethane, or chloroform) at ambient temperature. If the hydroxyl amine derivative exists as a salt, the acid can be neutralized by the addition of an amine base such as pyridine, collidine, or triethylamine.

Preparation of a compound of formula I wherein Z ≡ N represents a single bond

B. 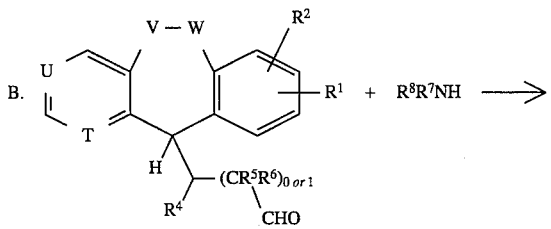

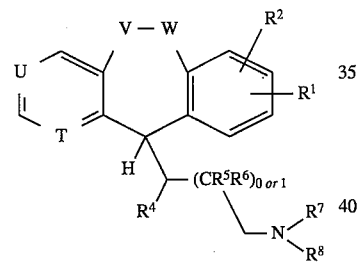

The reductive amination process is preferably carried out by treating the aldehyde with an amine (usually as a salt) in the presence of a reducing agent such as sodium cyanoborohydride and molecular sieves in a suitable solvent mixture of ether (e.g. diethyl ether, tetrahydrofuran, or dioxane) and protic solvent (e.g. methanol or ethanol) at ambient temperature.

C. 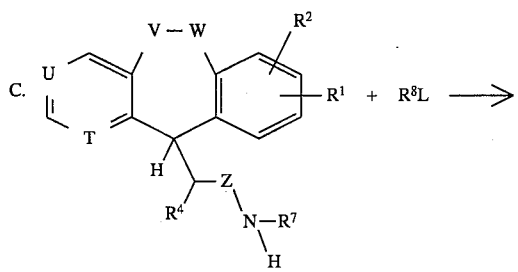

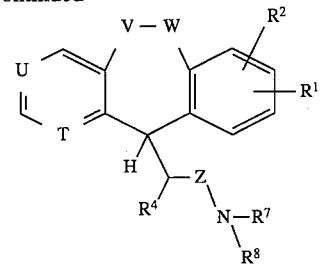

The process is preferably carried out by first adding an amine base (e.g. pyridine, collidine, or triethylamine) in an inert solvent such as chlorinated hydrocarbons (e.g. dichloromethane, 1,2-dichloroethane, or chloroform) or a strong base (n-butyl lithium, sodium hydride, potassium hydride, lithium diisopropyl amide, or potassium bis(trimethylsilyl)amide) in an inert solvent such as ether (e.g. diethyl ether, tetrahydrofuran, or dioxane) or polar aprotic solvent (e.g. N,N-dimethylformamide or N,N-dimethylacetamide) to the tricyclic amine under an inert atmosphere (nitrogen or argon). Subsequently, the alkylating or acylating agent $R^8L$ is added wherein L represents a good leaving group, e.g. L can be chloride, bromide, iodide, mesylate, or tosylate. Any suitable temperature can be used between −78° C. and 80° C.

D. 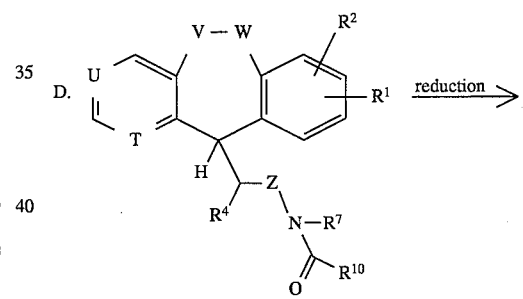

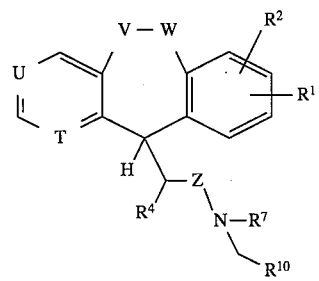

The process is preferably carried out with any suitable reducing agent (e.g. lithium aluminum hydride, alane, borane, or trichlorosilane) in an inert solvent such as ether (e.g. diethyl ether, tetrahydrofuran, or dioxane) at temperatures between 0° C. and 60° C.

E. 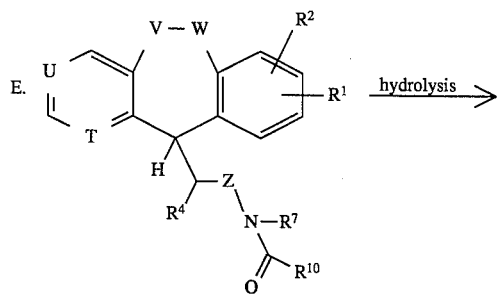

→ hydrolysis

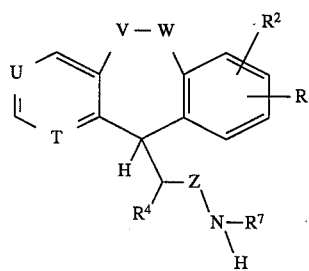

The process is preferably carried out by treating the amide or carbamate compound under basic (e.g. sodium hydroxide, potassium hydroxide, or sodium peroxide in water with ethylene glycol, methanol, ethanol, tetrahydrofuran, dioxane, or diglyme) or acidic (e.g. hydrochloric acid, sulfuric acid, or tosic acid in water with tetrahydrofuran, dioxane, or diglyme) conditions. Any suitable temperature can be used with preferable temperatures between 60° C. and 150° C.

F. 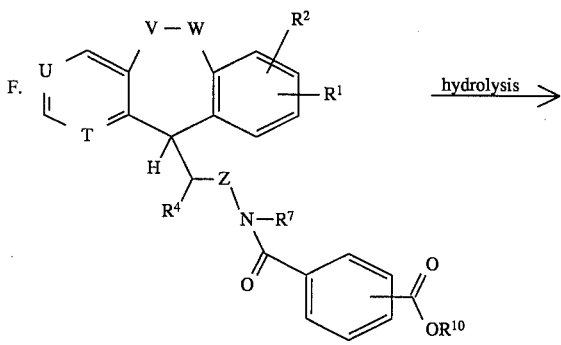

→ hydrolysis

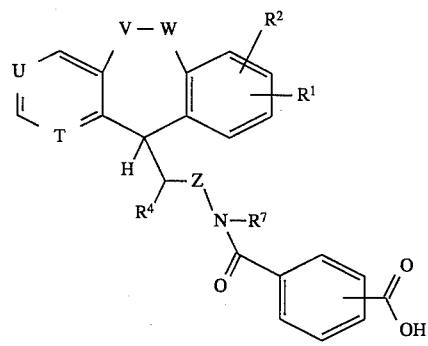

The process is preferably carried out by treating the tricyclic ester compound with a base (e.g. sodium hydroxide or potassium hydroxide) in water with tetrahydrofuran, dioxane, or diglyme. Any suitable temperature can be used with preferable temperatures between 25° C. and 100° C.

SPECIFIC PREPARATIVE EXAMPLES

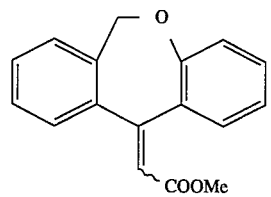

To synthesize an intermediate (step 1 of Scheme 1)

Washed sodium hydride (5.71 g of 60 wt %, 0.143 mol) two times with hexane under a nitrogen atmosphere. Added 170 mL of dry DMF, and cooled to 0° C. Added trimethyl phosphonoacetate (25.99 g, 0.143 mol) dropwise via addition funnel. Hydrogen evolution was observed. Stirred at 0° C for 15 mins. then at room temperature for 15 mins. Added 6,11-dihydro-dibenz[b,e]oxepin-11-one (15.00 g, 0.0714 mol) dissolved in 70 mL of dry DMF, and heated reaction mixture in a 80° C. oil bath for 45 hours. Cooled to room temperature, and added 250 mL of half saturated NH4Cl. Extracted with ethyl acetate. Washed combined organic extracts with saturated NaHCO$_3$, saturated NaCl, dried with MgSO$_4$, filtered, and evaporated. Purified crude product by flash chromatography on silica gel eluting with a gradient of 5% ethyl acetate-hexane, 7% ethyl acetate-hexane, then 20% ethyl acetate-hexane. Combined appropriate fractions and evaporated to give 3.16 g (21% yield) of starting ketone and 13.16 g (69% yield) of methyl 6,11-dihydro-dibenz[b,e] oxepin-11-ylidene acetate.

mass spectrum: (CI, isobutane) m/e 267 (M+1)

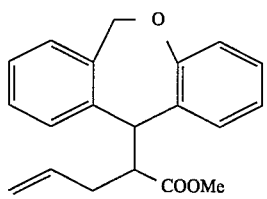

To synthesize an intermediate (step 2 of Scheme 1)

Dissolved methyl 6,11-dihydro-dibenz[b,e]oxepin-11-ylidene acetate (12.35 g, 0.0464 mol) in 160 mL of dry DMF and 40 mL of DMPU. Added tetra-n-butylammonium fluoride (2.00 g), 4 A molecular sieves, and then allyl trimethylsilane (15.90 g, 0.139 mol) dropwise via addition funnel. Stirred at room temperature for 90 mins. then added additional allyl trimethylsilane (5.30 g, 0.0464 mol). Stirred at room temperature for 16 hours. Added 50 mL of 9:1 by volume MeOH:1N HCl, 400 mL of water, and 200 mL of ethyl acetate. Filtered through celite, and separated layers. Extracted with ethyl acetate. Washed combined organic extracts with water, saturated NaCl, dried with MgSO$_4$, filtered, and evaporated. Purified crude product by flash chromatography on silica gel eluting with 5% ethyl acetate-hexane then 10% ethyl acetate-hexane. Combined appropriate fractions and evaporated to give 8.75 g (61% yield) of methyl 2-[6,11-dihydro-dibenzo[b,e]oxepin-11-yl]-pent-4-enoate.

mass spectrum: (Cl, CH₄) m/e 309(M+1)

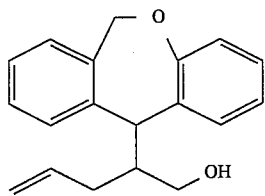

To synthesize an intermediate (step 3 of Scheme 1):

Dissolved methyl 2-[6, 11-dihydro-dibenzo[b,e]oxepin-11-yl]-pent-4-enoate (9.00 g, 0.0292 mol) in 100 mL of dry THF, and cooled to 0° C. under a nitrogen atmosphere. Added 1.0M lithium aluminum hydride in THF (29.2 mL, 0.0292 mol) via addition funnel. Stirred at room temperature for 45 mins. Added 1 mL of water, 1 mL of 1N NaOH, then 3 mL of water. Stirred at room temperature for 30 mins. then filtered through celite. Washed celite cake with ethyl acetate. Washed filtrate with saturated NaCl, dried with MgSO₄, filtered, and evaporated. Purified crude product by flash chromatography on silica gel eluting with 10% ethyl acetate-hexane then 25% ethyl acetate-hexane. Combined appropriate fractions and evaporated to give 6.78 g (83% yield) of 2-[6,11-dihydro-dibenzo[b,e]oxepin-11-yl]-pent-4-en-1-ol.

mass spectrum: (Cl, CH₄) m/e 281(M+1)

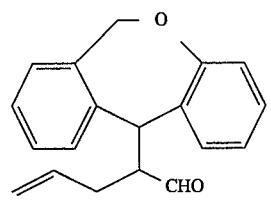

To synthesize an intermediate (Step 4 of Scheme 1)

Dissolved oxalyl chloride (3.83 g, 0.0302 mol) in 60 mL of dry dichloromethane, and cooled to −78° C. under a nitrogen atmosphere. Added DMSO (4.3 mL, 4.72 g, 0.0604 mol) dissolved in 15 mL of dry dichloromethane dropwise via addition funnel. CO and CO₂ evolution observed. Stirred at −78° C. for 10 mins. Added 2-[6,11-dihydro-dibenzo[b,e]oxepin-11-yl]-pent-4-en-1-ol (6.77 g, 0.0241 mol) dissolved in 50 mL of dry dichloromethane via addition funnel. Stirred at −78° C. for 15 mins. Added triethylamine (10.1 mL, 7.33 g, 0.0724 mol) via addition funnel, and warmed reaction mixture slowly to room temperature. Added 200 mL of water, and separated layers. Extracted aqueous solution with dichloromethane. Washed combined organic extracts with 0.5N HCl, saturated NaCl, dried with MgSO₄, filtered, and evaporated. Purified crude product by flash chromatography on silica gel eluting with 10% ethyl acetate-hexane then 15% ethyl acetate-hexane. Combined appropriate fractions and evaporated to give 6.44 g (96% yield) of 2-[6,11-dihydro-dibenzo[b,e]oxepin-11-yl]-pent-4-en-1-al.

mass spectrum: (Cl/CH₄) m/e 278 (M+)

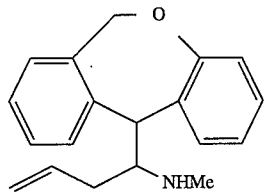

IA

For Compound IA:

Dissolved 2-[6,11-dihydro-dibenzo[b,e]oxepin-11-yl]-pent-4-en-1-al (5.0 g, 18.0 mmol) in 20 mL of dry THF and 60 mL of dry MeOH. Added 3 A molecular sieves, methylamine hydrochloride (6.1 g, 89.8 mmol), and then sodium cyanoborohydride (1.13 g, 18.0 mmol). Stirred at room temperature for 23 hours. Evaporated reaction mixture. Added 80 mL of saturated NaHCO₃ and 80 mL of dichloromethane. Filtered through celite. Separated layers. Extracted aqueous solution with dichloromethane. Dried combined organic extracts with MgSO₄, filtered, and evaporated. Purified crude product by flash chromatography on silica gel eluting with 5% MeOH—CH₂Cl₂. Combined appropriate fractions and evaporated to give 3.8 g (73% yield) of N-methyl-2-[6,11-dihydro-dibenzo[b,e]oxepin-11-yl]-pent-4-en-1-amine. Dissolved free base in ethyl acetate, and added one equivalent of maleic acid dissolved in ethanol. Evaporated to give maleate salt as a glass.

mass spectrum: (Cl, CH₄) m/e 294 (M+1 for free base)

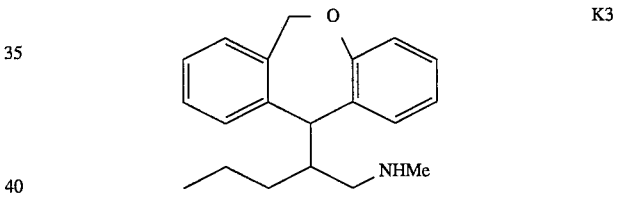

K3

For Compound K3:

Dissolved N-methyl-2-[6,11-dihydro-dibenzo[b,e]oxepin-11-yl]-pent-4-en-1-amine (0.50 g, 2.08 mmol) in 15 mL of absolute ethanol. Added 10 mg of 10% palladium on carbon catalyst, and stirred under atmospheric hydrogen balloon for 16 hours. Filtered through Celite, and washed with ethanol. Evaporated filtrate. Purified crude product by flash chromatography on silica gel eluting with 5% MeOH—CH₂Cl₂. Combined appropriate fractions, and evaporated to give 0.43 g (86% yield) of N-methyl-2-[6,11-dihydro-dibenzo[b,e]oxepin-11-yl]-pentanamine. Dissolved free base in ethyl acetate, and added one equivalent of maleic acid dissolved in absolute ethanol. Evaporated to foamy glass.

mass spectrum: (Cl, CH₄) m/e 296 (M+1 for free base)

The following compounds were obtained according to a similiar manner:

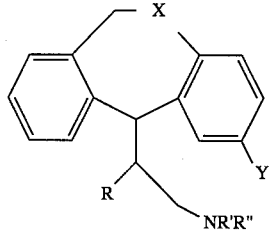

| X | Y | R | NR'R" | salt | Mass Spectrum |
|---|---|---|---|---|---|
| O | H | allyl | NMe$_2$ | maleate | (Cl, CH$_4$) m/e 308 (M + 1) |
| O | H | propyl | NMe$_2$ | maleate | (Cl, CH$_4$) m/e 310 (M + 1) |
| C | Cl | allyl | NHMe | maleate | (Cl, CH$_4$) m/e 326 (M + 1) |
| C | Cl | allyl | NMe$_2$ | maleate | (Cl, CH$_4$) m/e 340 (M + 1) |
| C | Cl | propyl | NHMe | maleate | (Cl, CH$_4$) m/e 328 (M + 1) |
| C | Cl | propyl | NMe$_2$ | maleate | (Cl, CH$_4$) m/e 342 (M + 1) |

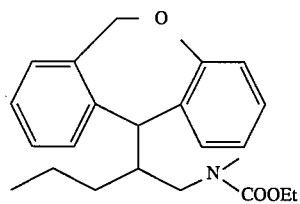

K4

For Compound K4:

Dissolved N-methyl-2-[6,11-dihydro-dibenzo[b,e]oxepin-11-yl]-pentanamine (0.50 g, 1.70 mmol)in 20 mL of dry THF. Added triethylamine (0.28 mL, 0.21 g, 2.02 mmol) and ethyl chloroformate (0.18 mL, 0.20 g, 1.86 mmol). Stirred at room temperature for 16 hours. Added water, and extracted with ether. Dried combined organic extracts with MgSO$_4$, filtered, and evaporated. Purified crude product by flash chromatography on silica gel eluting with dichloromethane. Combined appropriate fractions, and evaporated to give 0.45 g (73% yield) of ethyl [2-(6,11-dihydro-dibenzo[b,e]oxepin-1-yl)-pentyl]-methylcarbamate as a colorless oil.

mass spectrum: (Cl, CH$_4$) m/e 368 (M+1)

The following compounds were obtained according to a similiar manner:

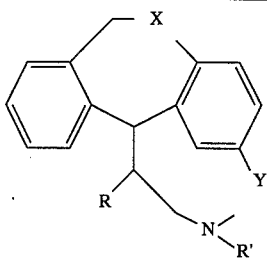

| X | Y | R | R' | mp | Mass Spectrum |
|---|---|---|---|---|---|
| O | H | propyl | acetyl | oil | (Cl, CH$_4$) m/e 338 (M + 1) |
| O | H | allyl | acetyl | oil | (FAB) m/e 336 (M + 1) |
| O | H | allyl | COOEt | oil | (FAB) m/e 366 (M + 1) |
| C | Cl | allyl | acetyl | oil | (Cl, CH$_4$) m/e 368 (M + 1) |

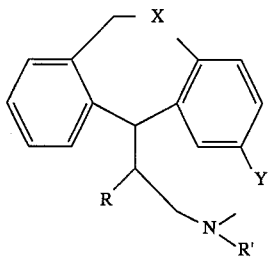

| X | Y | R | R' | mp | Mass Spectrum |
|---|---|---|---|---|---|

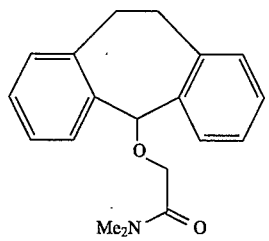

To synthesize an intermediate (step 6 of Scheme 2)

Washed sodium hydride (2.6 g, 64.6 mmol, 60 weight % in oil) two times with hexane under a nitrogen atmosphere. Added 50 mL of dry ether, and then added dibenzosuberol (13.6 g, 64.6 mmol) dissolved in 30 mL of dry ether followed by 2-chloro-N,N-dimethylacetamide (7.8 g, 64.6 mmol) dissolved in 20 mL of dry ether. Stirred at room temperature for 16 hours. Added water, and separated layers. Evaporated the organic solution, and triturated the residue with carbon tetrachloride and hexane. Filtered the white solid to give 13.79 g (72% yield) of 10,11-dihydro-5H-dibenzo[a,d]cyclohepten-5-yl-oxy-N,N-dimethylacetamide.

mp=73°–75° C. mass spectrum: (FAB) m/e 193 (M-Me$_2$NCOCH$_2$O)

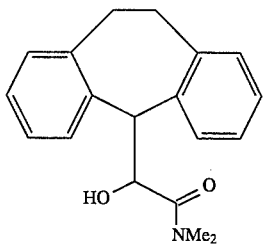

To Synthesize an intermediate (Step 7 of Scheme 2)

Washed sodium hydride (0.9 g, 22 mmol, 60 weight % in oil) two times with hexane under a nitrogen atmosphere. Added 100 mL of dry benzene and 10,11-dihydro-5H-dibenzo[a,d]cyclohepten-5-yl-oxy-N,N-dimethylacetamide (6.0 g, 20.3 mmol). Refluxed for 3 hours, and then cooled to room temperature. Carefully added water, and filtered to give the first crop of product. Separated the filtrate. Dried the organic solution with MgSO$_4$, filtered, and evaporated to an oil which was crystallized with ether. Filtered the solid, and combined with the first crop. Recrystallized product from isopropanol to give 3.59 g (60% yield) of 10,11-dihydro-N,N-dimethyl-5H-dibenzo[a,d]cycloheptene-5-glycolamide as a white solid.

mp=210°–214° C. mass spectrum: (FAB) m/e 296 M+1)

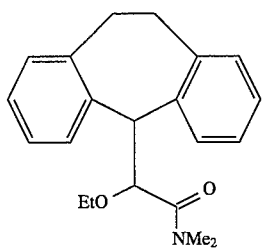

IE

For Compound IE:

Washed sodium hydride (2.4 g, 60 mmol, 60 weight % in oil) two times with hexane under a nitrogen atmosphere. Added 20 mL of dry dioxane and 10,11-dihydro-N,N-dimethyl-5H-dibenzo[a,d]cycloheptene-5-glycolamide (5.0 g, 16.9 mmol) dissolved in 350 mL of dry dioxane and 150 mL of dry DMF dropwise via addition funnel. Added ethyl iodide (9.54 g, 4.5 mL, 60 mmol), and refluxed the reaction mixture for 5 hours. Added minimal water (10 mL), and evaporated. Added dichloromethane, and separated layers. Dried the organic solution with MgSO$_4$, filtered, and evaporated. Triturated the crude product from petroleum

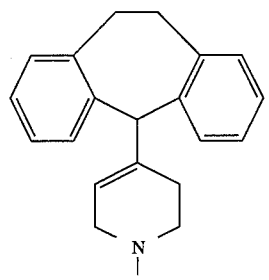

To synthesize an intermediate (step 12 of Scheme 3)

Dissolved 4-( 10,11-dihydro-5H-dibenzo[a,d]cyclohepten-5-ylidene)-1-methylpiperidine (12 g, 0.042 mol) in 250 mL of dry THF. Cooled to −78° C. under a nitrogen atmosphere. Added n-butyl lithium (18 mL of 2.5M in hexane) dropwise via addition funnel. Maintain temperature at 0° C. for 1 hour then recooled to −78° C. Added 21 mL of dry methanol, and let warm to room temperature. Added saturated NH$_4$Cl, and extracted with THF. Dried combined organic extracts with MgSO$_4$, filtered, and evaporated to give 11.3 g (94% yield) of 4-(10,11-dihydro-5H-dibenzo[a,d]cyclohepten-5-yl)-1-methyl-1,2,5,6-tetrahydropyridine as a white solid.

mp=96°–98° C. mass spectrum: (FAB) m/e 290 M+1)

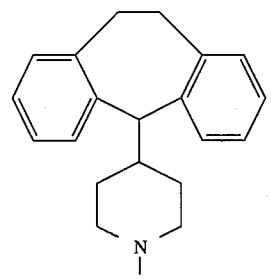

To synthesize an intermediate (step 13 of Scheme 3)

Dissolved 4-(10,11-dihydro-5H-dibenzo[a,d]cyclohepten-5-yl)-1-methyl-1,2,5,6-tetrahydropyridine (10.5 g, 0.036 mol) in 100 mL of glacial acetic acid and 60 mL of absolute ethanol. Added platinum oxide catalyst (1.5 g). Shake on Paar shaker at 60 psi of hydrogen pressure for 24 hours. Filtered, and washed catalyst with ethanol. Evaporated filtrate. Purified crude product by flash chromatography on silica gel eluting with 17% MeOH-EtOAc. Combined appropriate fractions, and evaporated to give 5.7 g (54% yield) of as a white solid.

mp=88°–89° C. ether to give 5.25 g (96% yield) of 2-ethoxy-2-[10,11-dihydro-5H-dibenzo[a,d]cyclohepten-5-yl]-N,N-dimethyl-acetamide as a white solid.

mp=86°–90° C. mass spectrum: (FAB) m/e 324 M+1)

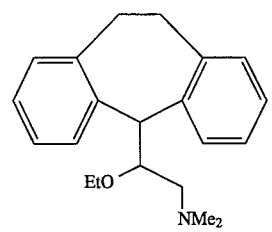

IB

For Compound IB:

Dissolved 2-ethoxy-2-[10,11-dihydro-5H-dibenzo[a,d]cyclohepten-5-yl]-N,N-dimethyl-acetamide (4.45 g, 13.8 mmol) in 100 mL of dry tetrahydrofuran, and added lithium aluminum hydride (0.6 g, 15.8 mmol) portionwise under a nitrogen atmosphere. Heated the reaction mixture at 60° C. for 2 hours. Cooled to 0° C., and carefully added 0.6 mL of water, 0.6 mL of 15 weight % NaOH, and then 1.8 mL of water in order to precipitate aluminum salts. Filtered precipitate, and washed with tetrahydrofuran. Evaporated filtrate, and purified the crude product by flash chromatography on silica gel eluting with 1:1 ethyl acetate:hexane. Combined appropriate fractions, and evaporated to give 3.44 g (81% yield) of β-ethoxy-10,11-dihydro-N, N-dimethyl-5 H-dibenzo[a,d]cycloheptene-5-ethanamine as a colorless oil. Dissolved free base in ethyl acetate, and added one equivalent of maleic acid dissolved in methanol. Evaporated, and added ether to precipitate maleate salt.

mp=138°–141° C. mass spectrum: (FAB) m/e 310 (M+1 for free base) mass spectrum: (FAB) m/e 292 M+1)

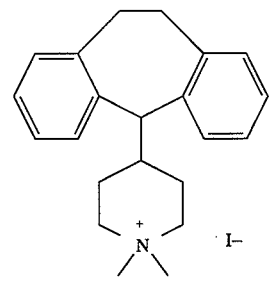

To synthesize an intermediate (step 14 of Scheme 3)

Dissolved 4-(10,11-dihydro-5H-dibenzo[a,d]cyclohepten-5-yl)-1-methyl-piperidine (1.0 g, 3.4 mmol) in 10 mL of methanol. Added iodomethane (0.71 g, 5.0 mmol), and stirred at room temperature for 18 hours. Filtered the precipitate to give 1.22 g (83% yield) of 4-(10,11-dihydro-5H-dibenzo[a,d]cyclohepten-5-yl)-1,1-dimethyl-piperidinium iodide as a white solid.

mp>300° C. mass spectrum: (FAB) m/e 306 (M-iodide for salt)

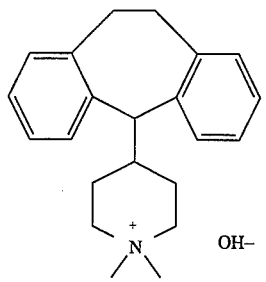

To synthesize an intermediate:

Mix 4-(10,11-dihydro-5H-dibenzo[a,d]cyclohepten-5-yl)-1,1-dimethyl-piperidinium iodide (1.14 g, 2.6 mmol) and silver oxide (3.48 g, 15.0 mmol) in 150 mL of methanol and 15 mL of water. Stirred at room temperature for 24 hours. Filtered, and evaporated filtrate to give 0.85 (100% yield) of 4-(10,11-dihydro-5H-dibenzo[a,d]cyclohepten-5-yl)-1,1-dimethyl-piperidinium hydroxide as a white solid.

mp=168°–171° C. mass spectrum: (FAB) m/e 306 (M-hydroxide for salt)

IC

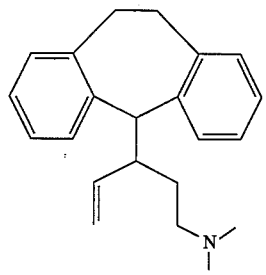

For Compound IC:

Heated 4-(10,11-dihydro-5H-dibenzo[a,d]cyclohepten-5-yl)-1,1-dimethyl-piperidinium hydroxide (0.84 g, 2.6 mmol) in a 180°–185° C. oil bath for 3 hours. Cooled to room temperature, and purified the crude product by flash chromatography on silica gel eluting with 10% MeOH—$CH_2Cl_2$. Combined appropriate fractions, and evaporated to give 0.3 g (37% yield) of 3-(10,11-dihydro-5H-dibenzo[a,d]cyclohepten-5-yl)-N,N-dimethyl-4-pentenamine as an oil. Dissolved free base in absolute ethanol, and added 28 weight % HCl-EtOH until acidic. Evaporated, and added 5:1 ether-:ethyl acetate. Let stand to precipitate hydrochloride salt.

mp=173°–175° C. mass spectrum: (Cl, $CH_4$) m/e 306 (M+1)

As mentioned above, the compounds of formula I exhibit good anti-TNF-α activity. The compounds of the invention are, therefore, useful when TNF-α activity is a factor in a given disease or disorder such as in the case of septic shock and various allergic diseases and inflammatory conditions.

The anti-TNF-α properties of the compounds of the present invention may be demonstrated by use of a standard in vitro pharmacological testing procedure as described below. This test procedure is a standard test used to determine anti-TNF-α activity and to evaluate the usefulness of said compounds for counteracting the biological effects of TNF-α.

1. In Vitro Study: Inhibition of LPS-Induced TNF-α Production From the Murine Cell Line WEHI-265

1) Cells (obtained from cell cultures containing $\leq 10^6$ cells/ml) are suspended at $0.2 \times 10^6$ cells/ml in complete medium (RPMI1640, with 10% FCS, $10^{-5}$M 2-ME, 2 mM glutan-fine and 10 mM HEPES buffer) and plated in CoStar 24 well plates (1.0 ml/well).

2) Compounds are dissolved in the appropriate vehicle at 400 times the concentration to be tested, and 5 μl of compound is added to the wells.

3) LPS (from *E. coli* 0111:B4) is diluted to 6 μg/ml and 1.0 ml is added to wells.

4) Plates are incubated 20–24 hours in 37° $CO_2$ incubator.

5) Supernatant fluids are collected and analyzed for TNF content as described in *J. Immunol.*, 142:3884.

The Results of this procedure are shown in TABLE 1 below.

TABLE 1

| COMPOUND | % INHIBITION AT 10 μM |
|---|---|
| IA | 54 |
| IB | 35 |
| IC | 46 |
| IE | 49 |
| IF | 4 |
| IG | 35 |
| IH | 23 |
| IJ | 34 |
| IK | 31 |
| IL | 49 |
| IM | 50 |
| IN | 28 |
| K1 | 15 |
| K2 | 54 |
| K3 | 73 |
| K4 | 48 |
| K5 | 46 |
| K6 | 64 |
| K7 | 39 |

In addition to the in vitro test described above, the following in vivo test was also performed on several of the compounds of the present invention. Although the individual reported values may be subject to a wide margin of error, collectively the in vivo data demonstrates that the compounds of the invention are inhibitors of TNF-α in a mammalian species.

1. In Vivo Study: Inhibition of LPS-Induced Serum TNF

Mice (C57Bl/6J males, 6–8 weeks of age) are dosed with the indicated compound (dissolved in CMC suspension vehicle; compounds are given orally or i.p. one hour before LPS challenge).

2) Mice are challenged with LPS (from *E. coli* 0111:B4; 50 μg i.p.).

3) Mice are bled 90 min after LPS challenge.

4) Sera are analyzed for TNF content by ELISA as described in *J. Immunol.* 142:3884.

Results are shown in TABLE 2 below.

TABLE 2

| COMPOUND | % INHIBITION AT 25 MG/KG |
|---|---|
| IA | 44 |
| IB | 25 |
| IE | 37 |
| IF | 24 |
| IG | 51 |
| IH | 30 |
| IL | 42 |
| K1 | 71 |
| K2 | 40 |
| K3 | 27 |
| K7 | 58 |

The effect of the compounds of the present invention against septic shock may be demonstrated by use of a standard pharmacological testing procedure as described below. This test procedure is a standard test used to determine activity against septic shock.

3. In Vivo Study: Inhibition of LPS/Galactosamine-Induced Lethality.
1) Mice (C57BI/6J males, 6–8 weeks of age) are dosed with the indicated compound (dissolved in CMC suspension vehicle; compounds are given orally or i.p. one hour before challenge with LPS and d-galactosamine).
2) Mice are challenged i.p. with a mixture of LPS (from E. coli 0111:B4; 100 ng) and d-galactosamine (8 mg).
3) Survival is determined 24 hours after challenge. See procedure published in J. Exp. Med. 165:657 (1987) Results are shown in TABLE 3 below.

TABLE 3

| COMPOUND | # DEAD/TOTAL AT 25 MG/KG |
|---|---|
| IB | 8/10 |
| IE | 10/10 |
| IF | 8/10 |
| IG | 7/9 |
| K1 | 1/10 |
| K2 | 7/10 |
| K5 | 10/10 |

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration. 15 Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to achieve relief of the symptoms.

DOSAGE FORMS

The following are examples of pharmaceutical dosage forms which contain a compound of the invention. As used therein, the term "active compound" is used to designate the compound

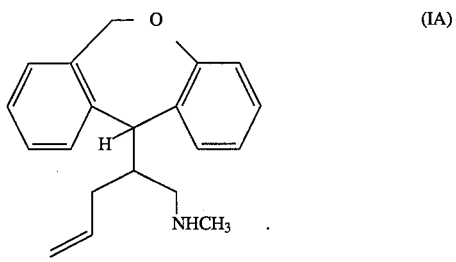

(IA)

The scope of the invention in its pharmaceutical composition aspect is not to be limited by the examples provided, since any other compound of Formula I can be substituted into the pharmaceutical composition examples.

Pharmaceutical Dosage Form Examples

EXAMPLE A

Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch, Food Grade | 45 | 40 |
| 5. | Magnesium Stearate | 3 | 7 |
|  | Total | 300 | 700 |

Method Of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B

Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
|  | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A compound of the Formula I:

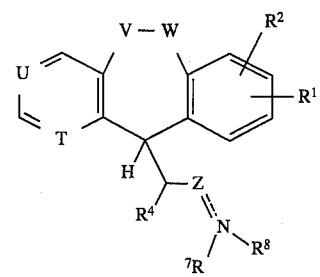

or a pharmaceutically acceptable salt or solvate thereof, wherein:

each of T and U represents CH;

one of V and W represents oxygen and the other represents —$CH_2$—; or each of V and W represent —$CH_2$—;

$R^1$ and $R^2$ are each independently selected from the group consisting of H and halogen;

$R^4$ is alkenyl or alkoxy;

--- represents an optional double bond;

--- when is a double bond, Z represents —CH=, or —$CH_2C(R^5)$=, wherein $R^5$ is H or lower alkyl; and $R^7$ and $R^8$ together represent $OR^9$;

--- when represents a single bond, Z represents —$CH_2$—, —CH=CH—, or —$CH_2C(R^5)(R^6)$—, wherein $R^5$ and $R^6$ are independently H or lower alkyl; and $R^7$ and $R^8$ are independently H, alkyl, alkenyl, alkynyl, aryl, alkaryl, aralkyl, cycloalkyl, —$OR^9$; —$C(O)OR^{10}$; —$CH_2C(O)OR^9$; —$C(O)R^{10}$; —$SO_2R^{10}$; —$(CH_2)_n$—$N(CH_3)_2$, where n is 2 to 4; —$(CH_2)_mO(CH_2)_jOH$, where m and j are independently 2 or 3;

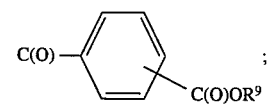

$R^9$ is H or lower alkyl; and $R^{10}$ is alkyl or aryl.

2. A compound according to claim 1, wherein $R^4$ is alkoxy.

3. A compound according to claim 2, wherein $R^4$ is ethoxy.

4. A compound according to claim 3, wherein $R^7$ and $R^8$ are independently H, alkyl, alkenyl, alkynyl, aryl, alkaryl, or aralkyl.

5. A compound according to claim 4 having the following structure:

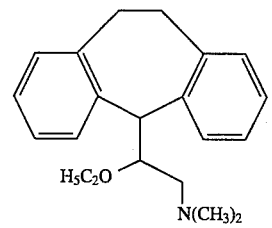

6. A compound according to claim 1, wherein $R^4$ is alkenyl.

7. A compound according to claim 6, wherein $R^7$ and $R^8$ are independently H, alkyl, alkenyl, alkynyl, aryl, alkaryl, or aralkyl.

8. A compound according to claim 7 having the following structure:

(IA)

9. A compound according to claim 7 having the following structure:

(IC)

10. A compound according to claim 1, wherein $\text{---}$ represents a single bond and Z represents $-CH_2-$.

11. A compound according to claim 1, wherein $R^7$ and $R^8$ are independently H or $-CH_3$.

12. A compound according to claim 1, wherein $\text{---}$ represents a single bond; Z represents $-CH_2-$; and $R^7$ and $R^8$ are independently H or $-CH_3$.

13. A compound according to claim 1, wherein each of T and U represents CH.

14. A pharmaceutical composition comprising an effective amount of a compound of claim 1 in combination with a pharmaceutically acceptable carrier.

15. A method of inhibiting tumor necrosis factor-α comprising administering to a mammal in need of such inhibition an effective anti-tumor necrosis factor amount of a compound of claim 1.

16. A pharmaceutical composition comprising an effective amount of a compound of the following structure IA in combination with a pharmaceutically acceptable carrier:

(IA)

17. A method of inhibiting tumor necrosis factor-α comprising administering to a mammal in need of such inhibition an effective anti-tumor necrosis factor amount of a compound having the structure IA in claim 16.

18. A method of inhibiting tumor necrosis factor-α comprising administering to a mammal in need of such inhibition an effective anti-tumor necrosis factor amount of a compound having the following formula K:

(K)

or a pharmaceutically acceptable salt or solvate thereof, wherein:

each of T and U represents CH;

one of V and W represents oxygen and the other represents $-CH_2-$; or each of V and W represents $-CH_2-$;

$R^1$ and $R^2$ are each independently selected from the group consisting of H and halogen;

$R^4$ is H or alkyl;

$\text{---}$ represents an optional double bond; when $\text{---}$ is a double bond, Z represents $-CH=$, or $-CH_2C(R^5)=$, wherein $R^5$ is H or lower alkyl; and $R^7$ and $R^8$ together represent $OR^9$;

$\text{---}$ represents a single bond, Z represents $-CH_2-$, $-CH=CH-$, or $-CH_2C(R^5)(R^6)-$, wherein $R^5$ and $R^6$ are independently H or lower alkyl; and $R^7$ and $R^8$ are independently H, alkyl, alkenyl, alkynyl, aryl, alkaryl, aralkyl, cycloalkyl $-OR^9$; $-C(O)OR^{10}$; $-CH_2C(O)OR^9$; $-C(O)R^{10}$; $-SO_2R^{10}$; $-(CH_2)_n-N(CH_3)_2$, where n is 2 to 4; $-(CH_2)_mO(CH_2)_jOH$, where m and j are independently 2 or 3;

$R^9$ is H or lower alkyl; and $R^{10}$ is alkyl or aryl.

19. A method according to claim 18 wherein, in the compound of formula K, $\text{---}$ represents a single bond and $R^7$ and $R^8$ are independently H or alkyl.

20. A method according to claim 18 wherein the compound of formula K has the following structure:

(K1)

21. A compound according to claim 1 having a structure selected from the group of structures consisting of:

(IA) 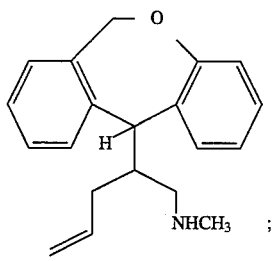
(IB) 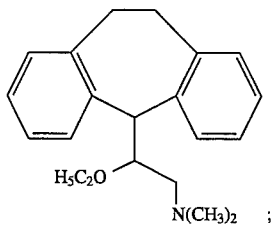
(IC) 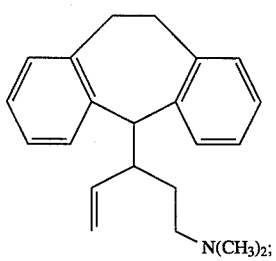
(IG) 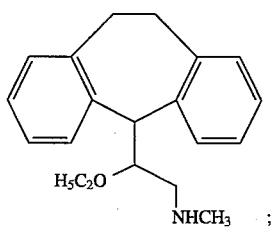
(IH) 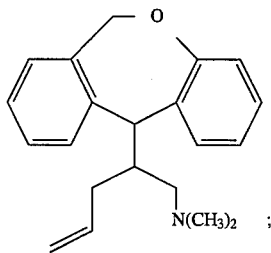
(IJ) 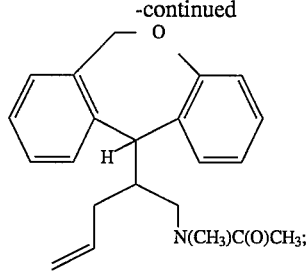
(IK) 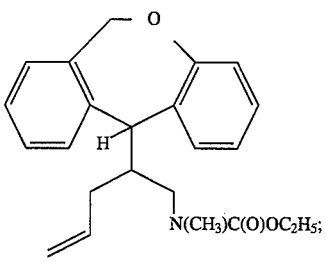
(IL) 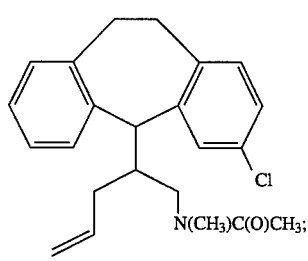
(IM) 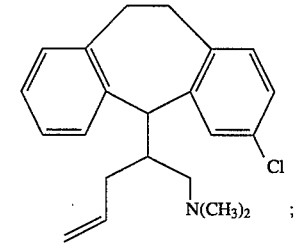
and
(IN) 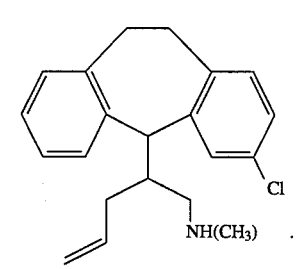
* * * * *